United States Patent [19]
Rei et al.

[11] Patent Number: 4,789,692
[45] Date of Patent: Dec. 6, 1988

[54] RESIN-IMMOBILIZED BIOCIDES

[75] Inventors: Nuno M. Rei, Boxford; Joel A. Gribens, Framingham, both of Mass.

[73] Assignee: Morton Thiokol, Inc., Chicago, Ill.

[21] Appl. No.: 895,760

[22] Filed: Aug. 12, 1986

[51] Int. Cl.⁴ ............................ C08J 3/22; C08K 5/15
[52] U.S. Cl. ................................... 523/122; 523/351;
524/83; 524/89; 524/109; 524/110; 524/104
[58] Field of Search .................... 106/18.32, 18.34;
523/122, 351; 424/78, 83

[56] References Cited

U.S. PATENT DOCUMENTS

| Re. 29,409 | 9/1977 | Yeager | 428/78 |
|---|---|---|---|
| 2,792,394 | 6/1957 | Himel et al. | 260/247.1 |
| 2,951,766 | 9/1960 | White | 106/15 |
| 3,228,830 | 1/1966 | McFadden et al. | 167/42 |
| 3,257,351 | 6/1966 | Kraus et al. | 260/41 |
| 3,288,674 | 11/1966 | Yeager | 167/42 |
| 3,318,769 | 5/1967 | Folckemer et al. | 167/42 |
| 3,551,192 | 12/1970 | Reinert | 523/127 |
| 3,635,994 | 1/1972 | Domenico | 260/294.8 F |
| 3,694,543 | 9/1972 | Needham et al. | 424/30 |
| 4,086,297 | 4/1978 | Rei et al. | 260/859 |
| 4,394,459 | 7/1983 | Rys-Sikora | 521/84 |
| 4,624,679 | 11/1986 | McEntee | 523/122 |
| 4,661,528 | 4/1987 | Rei | 523/122 |
| 4,663,077 | 5/1987 | Rei et al. | 523/122 |
| 4,663,359 | 5/1987 | Rei | 523/122 |

FOREIGN PATENT DOCUMENTS 0174638 10/1984 Japan ..................... 523/122

Primary Examiner—John C. Bleutge
Assistant Examiner—David W. Woodward
Attorney, Agent, or Firm—Wayne E. Nacker; Gerald K. White

[57] ABSTRACT

For providing biocides in concentrated, immobilized form to an end use resin composition containing a primary thermoplastic resin with which the primary resin is incompatible at high concentrations, solid biocide resin concentrates are provided which immobilize high concentrations of biocide. The solid biocide resin concentrates may contain an alloy of two thermoplastic resins, one of which is substantially identical to the primary resin and one of which enables incorporation and immobilization of high concentrations of biocide in the solid biocide resin concentrates. The solid biocide resin concentrate may contain, in whole or in part, a thermoplastic copolymer having mer units such as are present in the primary resin in addition to dissimilar mer units which enhance compatibility of the biocide with the copolymer. OBPA-containing solid resin concentrates for adding to an end use resin composition in which polyethylene is the primary resin may contain polyethylene plus a second thermoplastic resin in which OBPA is generally compatible and/or a copolymer containing both ethylene and acrylic acid mer units and/or a terpolymer containing ethylene, vinyl acetate and carbon monoxide mer units. Ethylene/acrylic copolymers and ethylene/vinyl acetate/carbon monoxide terpolymers are each useful for forming solid biocide resin concentrates that are miscible with a wide variety of thermoplastic resins.

19 Claims, No Drawings

4,789,692

RESIN-IMMOBILIZED BIOCIDES

The present invention is directed to compositions in which biocides are stably incorporated into solid thermoplastic resins.

BACKGROUND OF THE INVENTION

It is known to protect various thermoplastic resin compositions against fungal or bacterial attack by incorporating a microbiocide therein to prevent the deterioration of articles formed from the resin compositions. Microbiocides inhibit growth of bacteria or fungi by acting upon the cell wall or upon cell proteins, e.g., by attacking disulfide bonds. In order for the microbiocide to be effective in the resin composition, it is necessary that it be compatible with the components of the composition and be uniformly dispersible in the resin composition. The biocide must be carried by the resin composition in a manner that it remains biologically active against microorganisms, and, in particular, must be available at the surfaces, including internal pore surfaces. Incorporation of biocides in resin compositions is generally effective only in compositions in which the biocide is able to slowly migrate to the surfaces. In some cases, the biocide migrates slowly through amorphous regions of the polymer. In other cases, biocide migration is facilitated by plasticizers which are included along with the polymeric resins in end use resin compositions. As the biocide at the surfaces is used up through action against microorganisms, additional biocide migrates to the surfaces. Although biocides may be highly toxic chemicals, their low concentration in the end use product and their retention by the resin composition ensure that biocides in the end use product pose no hazard to humans or animals.

Biocides must be available in a form that is readily dispersible into the formulation mix from which the resin composition is fabricated. The powdered or crystalline form in which many useful biocides are commercially available are readily dispersible; however, at the site of mixing, powdered or crystalline biocides pose a substantial environmental and health hazard if powder or crystal fines are dispersed into the atmosphere. Furthermore, powder, or powdered fines, if dispersed into the atmosphere, represent a potential explosive hazard.

Recognizing the toxicity problem of biocides in powder or crystalline form, U.S. Pat. No. Re. 29,409, the teachings of which are incorporated herein by reference, teaches dissolving biocides in a liquid solvent which may be added to the formulation mixture from which the end use resin composition is fabricated. Although liquid dispersions may be safely used at the site of preparing an end use resin composition, careless use or disposal of the liquid may still pose environmental and health hazards.

U.S. Pat. No. 4,086,297 issued Apr. 25, 1978 to Rei, et al., the teachings of which are incorporated herein by reference, describes solid thermoplastic biocide resin concentrates containing immobilized biocides. These solid biocide resin concentrates contain relatively high concentrations of biocides and may be added to the formulation mixture from which the end use resin composition is prepared in an amount sufficient to provide the desired end use biocide concentration. The solid biocide resin concentrates, which are typically provided in the form of small pellets, can be handled freely, posing substantially no health or environmental threat. Such pellets are even safe for direct skin contact. Although biocides are sufficiently immobilized and inactive in the solid biocide resin concentrates in softer end use resin compositions, the low concentration biocides at the surface have biological activity, and gradual and continuous migration to surfaces ensures continuous biological activity. Where practical, solid biocide resin concentrates represents a preferred manner of providing biocides to producers of end use thermoplastic products.

In order that solid thermoplastic resin compositions be a practical means of providing biocides to the site of preparation of the end use thermoplastic resin composition, the biocide must be stably incorporated into the solid resin composition at concentrations substantially above end use concentrations. Generally, the concentration of the biocide in the solid biocide resin concentrate must be between about 20 and about 500 times the concentration of the biocide in the end use resin composition, and typically the concentration of the biocide in the solid biocide resin concentrate is about 100 times the end use concentration, enabling the solid biocide resin concentrate to be added to the non-fabricated resin compound at one part per hundred of the total amount of thermoplastic resin added to the non-fabricated resin compound. As a practical matter, the concentration of biocide in the solid biocide resin concentrate cannot be too low, or excessive amounts of thermoplastic resin must be pre-processed to contain a sufficient amount of biocide. Also as a practical matter, the concentration of the biocide in the solid biocide resin concentrate should not be excessively high, in which case, only a very small amount of the pre-processed solid biocide resin concentrate would be added to the non-fabricated compound, posing substantial problems with respect to obtaining a homogenous blend.

It has been found that certain biocides are not stably incorporated into particular resins at the concentrations required for providing a preprocessed solid biocide resin concentrate. In particular, an important and widely used biocide, 10,10'-oxybisphenoxarsine, (OBPA) is not sufficiently compatible in polyethylene resin for a practical polyethylene/OBPA solid biocide resin concentrate to be produced. For most end uses, in order to provide adequate biocidal protection for the end use product, OBPA is present at about 0.05 weight percent of thermoplastic resins, requiring that a solid biocide resin concentrate contain at least about 1.0 wt % (at a 20×concentration) and preferably about 5 wt % (at a 100×concentration). In fact, OBPA an only be stably incorporated in solid polyethylene resin concentrate at up to about 0.2 wt. percent. At higher OBPA concentrations, OBPA blooms or spews to the surface of polyethylene. Such a biocide bloom represents a health hazard to anyone handling the solid biocide resin concentrate.

A 0.2 weight percent admixture of OBPA with polyethylene resin would require a one part per four (total) admixture of solid biocide resin concentrate with additional polyethylene resin in the end use resin compound formulation, a commercially unacceptable requirement. This would require pre-processing large quantities of thermoplastic polyethylene resin, and there is little commercial advantage in doing so.

OBPA is stably incorporated at desirable 5 wt. percent levels in other polymeric resins, such as polystyrene and polypropylene; however, these resins differ in physical properties from polyethylene. OBPA-containing resins of polypropylene, polystyrene and other previously prepared solid biocide resin concentrates represent an adulteration to a polyethylene end use product and tend to significantly affect the physical properties of the end use product. Also, due to their respective melt indicies, these polymers do not mix easily with polyethylene. Accordingly, such solid biocide resin concentrates may be unsuitable for use in a resin compound from which is fabricated an end use resin composition having particular properties. Even where end use properties are not highly critical, the manufacturer of the end use resin composition may be reluctant to adulterate the polyethylene with the foreign polymer of the solid biocide resin concentrate, which typically represents about 1% of the total thermoplastic polymeric resin.

It is desired to have new solid thermoplastic biocide resin concentrates in which biocides are stably immobilized at commercially desirable concentrations. In particular, it is desired to have sold biocide resin concentrates in which OBPA is stably immobilized at commercially acceptable concentrations, which solid biocide resin concentrates include a resin component or combination of components which more closely resemble and are more closely compatible with polyethylene in end use resin compositions than are presently available OBPA-containing solid resin compositions. It is also desirable to provide solid biocide resin concentrates which can be mixed with a variety of different polymers.

SUMMARY OF THE INVENTION

Biocides, which cannot be stably immobilized in solid biocide resin concentrates matching the primary resin component of the end use resin composition at commercially acceptable concentrations, are immobilized in a solid biocide resin concentrate which closely resembles the primary resin component of the end use resin composition and which is compatible with commercially useful levels of biocides.

Biocide-containing solid biocide resin concentrates may contain a first thermoplastic resin substantially identical to the primary resin component of the end use resin composition but in which the biocide cannot be stably immobilized plus a second thermoplastic resin in which the biocide can be stably incorporated. The second thermoplastic resin is present at a sufficiently high weight percent that the biocide is stably incorporated into the alloyed resins of the solid biocide resin concentrates.

Copolymer, terpolymers, etc. resins are provided for stably immobilizing biocides. The copolymers contain (A) mer units identical to those of the resin component of the end use resin composition and (B) additional mer units which enhance compatibility with the biocide. The solid biocide resin concentrates may also be an alloy of (1) a copolymer, terpolymer, etc. with (A) mer units identical to the mer units of the primary resin component of the end use resin composition and (B) dissimilar mer units which enhance biocide compatibility plus (2) a resin substantially identical to the resin of the end use resin composition.

In accordance with a particular aspect of the present invention, OBPA at commercially acceptable levels is stably incorporated in copolymers of acrylic acid and ethylene and mixtures of the copolymer and polyethylene. OBPA at commercially acceptable levels may also be stably incorporated in mixtures of polyethylene and a second resin, such as polypropylene or polystyrene. Copolymers of ethylene and acrylic acid and terpolymers of ethylene, vinyl acetate and carbon monoxide are each found to form solid biocide resin concentrates that are useful carriers of biocides into a wide variety of thermoplastic resin compositions.

DETAILED DESCRIPTION OF CERTAIN PREFERRED EMBODIMENTS

The following terms are used herein as follows:

"Solid biocide resin concentrate"—a concentrate comprising one or more thermoplastic resins and a relatively high concentration of a biocide, the biocide being immobilized and generally inactive in the thermoplastic resin(s).

"Primary resin"—the thermoplastic polymeric material which comprises the major polymeric component of the end use resin composition.

"End use resin composition"—a fabricated material containing one or more thermoplastic resins, optional additives such as plasticizers, and a minor proportion of a biocide-containing solid resin composition.

"End use resin compound"—a non-fabricated mixture containing the components which comprise the end use resin composition, including an appropriate minor amount of the biocide-containing solid biocide resin concentrates, primary resin, and optional additives.

In accordance with one aspect of the present invention, in cases where a particular biocide cannot be stably incorporated and immobilized in a solid thermoplastic resin identical to or closely analogous to the primary resin used in the end use resin composition, the biocide is stably incorporated and immobilized in (1) a resin alloy comprising a first thermoplastic resin identical to or substantially identical to the primary resin plus a second resin in which the biocide is readily incorporated and immobilized, and/or (2) a thermoplastic copolymer resin having (A) mer units such as are also contained in the primary resin plus (B) additional mer units which promote stable incorporation and immobilization of the biocide therein.

Herein, when it is stated that a thermoplastic resin is "substantially identical" to the primary resin, it is meant that at least about 90 molar percent of the mer units which comprise the mer units of the "substantially identical" thermoplastic resin are identical to the mer units of the primary resin. Thus, polyethylenes of substantially different molecular weight are considered to be substantially identical for purposes of the present invention.

A solid biocide resin concentrate may be added to the end use resin compound from which the end use resin composition is fabricated without posing any health hazard to workers and without posing any environmental hazard. A solid biocide resin concentrate formulated in accordance with the present invention is incorporated into the end use resin compound with substantially less effect on the physical properties of the end use resin composition than a prior art solid biocide resin concentrate in which the biocide-containing resin is substantially dissimilar to the primary resin.

Thermoplastic resins used to form the solid biocide resin concentrates in accordance with the invention preferably should be rigid at room temperature, i.e., have glass transition temperatures ($T_g$'s) well above room temperature, preferably at least 80° C. and more preferably at least 100° C. This contrasts with end use resin compositions which preferably are non-rigid, having $T_g$'s below room temperature and permit biocide migration. Thermoplastic resins for forming the solid resin compositions must substantially immobilize the biocide and be compatible with and mix well with the primary resin used in the end use resin compound. Thermoplastic resins used in the solid biocide resin concentrates desirably have minimal effects on the physical properties of the end use resin compositions so that a manufacturer producing end use resin compositions and products formed therefrom may use the solid biocide resin concentrates with assurance that the physical properties of the end use composition will be substantially unchanged. For processing considerations, it is desired that the thermoplastic resins have relatively low melt processing temperatures, preferably below about 150° C. and more preferably below about 135° C. Low melt processing temperatures help to ensure that the solid biocide resin concentrates can be melted and blended with the other components of the end use resin compound without degradation of the compound components, including the primary resin, the biocide and optional additives, such as plasticizers.

Solid biocide resin concentrates in accordance with the present invention include biocide-containing resin alloys of a first polymer identical to or substantially identical to the primary resin of the end use resin composition plus a second resin in which relatively high concentrations of the biocide are compatible, and which when alloyed with the first resin provides a solid alloy biocide resin concentrate in which a desirably high concentration of the biocide is incorporated and immobilized. The second resin, of course, represents an adulteration of the end use resin compound, but the amount of adulteration is reduced by the amount of the first resin which is incorporated in the alloy, and, desirably, as much of the first resin is incorporated in the alloy as is consistent with stable biocide incorporation and immobilization. The second resin is selected for being sufficiently compatible with the biocide such that when alloyed with at least about 50 wt % of the first resin, the particular biocide is stably incorporated and immobilized therein. The greater amount of the first resin which can be incorporated into the biocide-containing alloy as facilitated by the second resin, the less adulteration of the end use resin composition and the more generally commercially desirable the solid biocide-containing alloyed resin concentrate.

The primary resins of which this invention speaks is typically a homopolymer because problems of biocide/thermoplastic resin compatibility are more prevalent with homopolymers; however, where the primary resin is a copolymer and biocide/resin compatibility problems are encountered, the invention provides solid biocide resin concentrates suitable for carrying biocides to compounds containing copolymeric primary resins.

It is important to distinguish (A) alloying a second resin with a first resin to enable incorporation and immobilization of the biocide in the resin alloy at a selected concentration from (B) preparing a solid biocide resin concentrate containing only the second resin and an even higher concentration of the biocide, which would require adding a lesser amount of the more concentrated solid biocide resin concentrates to the end use resin compound. In either case, adulteration of the end use resin compound by the foreign (second) resin is minimized. However, mixing considerations require that a sufficient quantity of the solid biocide resin concentrate be added, particularly in rapid mixing procedures; otherwise incomplete dispersion of the biocide throughout the end use resin compound may occur.

By way of hypothetical illustration, assume that biocide concentration of 0.05 wt. % in the end use composition is desired. Assume further that the concentration of biocide incorporation into a solid biocide resin concentrate is dependent upon the wt. % of the second resin such that (1) 5% incorporation of biocide is achieved using an alloy containing 10 wt % of the second resin, and (2) that a 50% biocide concentration is obtainable in neat second resin. (Herein, unless otherwise noted, all percentages are by weight, and weight percentages of the solid biocide resin concentrate are calculated relative to total weight of the resin or resins therein, exclusive of the biocide). To achieve an end use biocide concentration of 0.05% (1) the alloyed solid biocide resin concentrate would be added at one part per hundred parts of total resin (1 part added to 99 parts), whereas (2) the neat solid biocide resin concentrate would be added in the compound at one part per thousand total resin. Addition of the alloy at 1 part per hundred total is clearly preferred for mixing considerations. At one part per thousand, difficulties are generally encountered in mixing to achieve a homogeneous end use resin compound. Furthermore, manufacturers who prepare end use resin compounds may strive for consistency, preferring to add a similar weight percent of biocide-containing concentrate for each formulation, e.g., one part per hundred total, to avoid confusion of the compounders and reduce the likelihood of formulation errors. Preparing an alloy is further advantageous relative to a neat solid biocide resin concentrate of higher biocide concentration because the second resin is at least partly pre-dissolved in the first resin, further enhancing blending of the second resin and the biocide in the end use resin compound.

Of particular interest herein, is the stable incorporation of OBPA in solid biocide resin concentrates suitable for admixture into a polyethylene end use resin compound. Polyethylene in itself is an unsuitable carrier for OBPA because OBPA cannot be stably incorporated and immobilized above about 0.2 weight percent, which for a desired end use OBPA concentration of 0.05 weight percent would require an unacceptable 1:3 weight ratio of OBPA-containing neat polyethylene solid biocide resin concentrate to primary polyethylene resin in an end use compound.

In referring to OBPA, which is a commercially available and widely used biocide in thermoplastic compositions, similar considerations apply to derivatives of OBPA, such as those described in U.S. Pat. No. 3,228,830. Solid polyethylene preparations prepared with higher concentrations of OBPA spew OBPA to the surface, whereupon the composition represents a hazard to anyone contacting the composition.

With respect to providing a solid alloy biocide resin concentrate for carrying OBPA into a polyethylene end use resin compound, the first resin is polyethylene, and the second resin is selected from the group consisting of ethylene/acrylic acid copolymers, polypropylene, polystyrene, polyvinyl chloride/polyvinyl acetate (PVC/PVA) 85:15, polyacrylic acid and a terpolymer of ethylene, vinyl acetate and carbon monoxide, such as sold under the trademark Elvaloy by duPont. It is also contemplated that the second resin include mixtures of these resins; however, increasing the numbers of resins in the solid alloy biocide resin concentrate tends to complicate the system and reduce predictability of physical properties of end use biocide resin compositions; thus, alloy concentrates containing a second resin mixture are generally considered to be less desirable than are alloy concentrates containing a homogenous second resin.

For OBPA, it is generally desired that the solid biocide resin concentrate contain about 5 wt. % OBPA in order to achieve an end use concentration of 0.05 wt. % OBPA with a 1:99 dilution; however, 1 wt. % solid OBPA resin concentrates may be prepared and used as a 1:19 dilution.

Table 1 below lists the minimum weight percentages of the second alloying polymers for preparing stable OBPA/polyethylene/second biocide resin alloy concentrates with 5% and 1% OBPA concentrations. (Herein, weight percentages of biocides are calculated relative to the total weight of the thermoplastic resins.) It is to be understood, that while the resins are described herein in terms of their mer unit structure, e.g., polypropylene, polystyrene etc., that these terms encompass thermoplastic resins of various molecular weights and physical properties. Nevertheless, as OBPA compatibility is primarily a function of resin material mer units, Table 1 provides good general minimum values of second resin concentration.

TABLE 1

| Alloying resin | 5% OBPA | 1% OBPA |
| --- | --- | --- |
| Ethylene-acrylic acid copolymer | 25 wt percent | 5 wt percent |
| polypropylene | 30 wt percent | 6 wt percent |
| polystyrene | 25 wt percent | 5 wt percent |
| PVC/PVA 85:15 | 20 wt percent | 4 wt percent |
| Elvaloy | 25 wt percent | 5 wt percent |

In accordance with another aspect of the invention, where the biocide cannot be stably incorporated at high enough concentrations in a resin that is the same or substantially the same as the primary resin of the end use resin compound, solid biocide resin concentrates are prepared comprising the biocide and a copolymer resin having (A) a first mer unit which is a mer unit of the primary resin of the end use resin compound and (B) a second mer unit which enhances the compatibility of the biocide with the copolymer resin. The copolymer resin may be used (1) neat in the solid biocide resin concentrates along with the biocide or (2) as the second resin in a solid biocide resin alloy concentrate in which the first resin is identical to or substantially identical to the primary resin of the end use resin compound. Copolymers in accordance with this invention typically contain between about 3 and about 75 molar percent of mer units dissimilar to those of the primary resin. The solid biocide resin concentrates, including concentrates with resin mixtures, typically contains between about 3 and about 50 molar percent dissimilar mer units. Because the copolymer contains mer units found in the primary resin, it is generally a less detrimental, i.e., property-altering, adulteration of the end use resin composition than is a resin which contains none of the mer units found in the primary resin.

In accordance with a specific preferred embodiment of the invention, solid biocide resin concentrates comprise OBPA stably incorporated and immobilized in (A) a copolymer of ethylene and acrylic acid or (B) in an alloy of polyethylene and the copolymer. The ethylene mer units of the copolymer correspond to the mer units of polyethylene while the acrylic acid mer units provide good compatibility of the copolymer with OBPA. Preferred copolymers for use with OBPA comprise from about 3 to about 25 molar percent acrylic acid mer units, balance ethylene mer units and more preferably between about 15 and about 25 molar percent acrylic acid mer units. The copolymer may be alloyed with polyethylene according to the concentration of OBPA desired in the solid biocide resin concentrate. The amount of polyethylene which may be alloyed with the copolymer and still provide compatibility of the OBPA is dependent upon the molar percentage of acrylic acid mer units in the copolymer. A copolymer having 25 molar percent acrylic acid mer units may be alloyed with up to about 35 wt. % polyethylene and stably retain 5 wt. % OBPA. If a 2½% OPBA composition is required, the copolymer having 25 molar percent acrylic acid mer units may be alloyed with up to about 50 weight percent polyethylene.

In general, for a system using either ethylene/acrylic acid copolymer alone or an alloy of the copolymer plus polyethylene, there exists a threshold minimum molar percentage of acrylic acid mer units, calculated according to total mer units of the copolymer or copolymer/polyethylene alloy, that is necessary to retain the OBPA. Generally, for OBPA concentrations in the 1 to 5 wt. percent range, the copolymer or copolymer/polyethylene alloy should contain at least about 4 molar percent acrylic acid mer units per each wt. percent of OBPA to be incorporated in the solid resin composition. Thus to provide a 5 wt. % OBPA solid biocide resin concentrate, the copolymer or copolymer/polyethylene alloy should contain at least about 20 molar percent acrylic acid mer units. It is not desirable to provide acrylic acid mer units much in excess of what is required for OPBA compatibility because acrylic acid mer units represent an adulteration of the polyethylene in the end use resin compounds. The threshold levels of acrylic acid mer units are only an approximation, depending upon the melt indicies and other specific characteristics of the copolymer and the polyethylene; for example, polyethylenes to which OPBA may be added range in melt indicies from about 10 to about 300. The actual relative amounts of copolymer, OPBA and polyethylene in a particular solid biocide resin concentrate must be empirically determined.

In accordance with a further aspect of this invention, it is found that in addition to the specific use of copolymers of ethylene and acrylic acid as a carrier of OBPA into solid resin concentrates and end use polyethylene compositions, copolymers of ethylene and acrylic acid are generally useful as carriers of biocides into end use thermoplastic resin compositions. Ethylene/acrylic acid copolymers having between about 3 and about 25 molar percent acrylic acid mer units exhbit a surprising range of miscibility and compatibility with a wide range of thermoplastic polymers, including but not limited to polyethylene, nylon, polystyrene, PVC polycarbonate, polypropylene, polyvinyl chloride/polyvinyl acetate 85:15, polyvinyl acetate, polymethyl methacrylate and related compounds.

In accordance with still a further aspect of this invention, it is found that terpolymers of ethylene, vinyl acrylate and carbon monoxide are generally useful as carriers of biocides into end use thermoplastic resin compositions. Such ethylene/vinyl acetate/carbon monoxide terpolymers have between about 40 and about 75 molar percent ethylene mer units, between about 20 and about 30 molar percent vinyl acetate mer units and between about 5 and about 35 molar percent carbon monoxide mer units. Terpolymers of this type are described in U.S. Pat. No. 4,394,459 issued July 19, 1983 to Rys-Sikora, the teachings of which are incorporated herein by reference. Ethylene/vinyl acetate/carbon monoxide terpolymers exhibit a surprising range of miscibility and compatibility with a wide range of thermoplastic polymers, including but not limited to polyethylene, nylon, polystyrene, PVC, polycarbonate, polypropylene, polyvinyl chloride/polyvinyl acetate 85:15, polyvinyl acetate, polymethyl methacrylate and related compounds.

Because of this wide range of miscibility, thermoplastic solid biocide resin concentrates comprising a biocide plus either ethylene/acrylic acid copolymer or ethylene/vinyl acetate/carbon monoxide terpolymer are generally universally useful for carrying the biocide to the end use thermoplastic resin compound. In some cases, the copolymer or terpolymer may affect properties of the end use composition; nevertheless, when end use properties are not highly critical, a manufacturer of a variety of end use thermoplastic compositions may wish to use a universally acceptable biocide carrier.

In forming solid biocide resin concentrates using ethylene/vinyl acetate/carbon monoxide terpolymers, the processing temperatures or shear forces influence the nature of the final product. At higher temperatures and/or shear forces, a more brittle concentrate is produced which may be pelletized, e.g., by extruding a continuous cylindrical strand and cutting the strand into small pieces. At lower temperatures and/or shear forces, a more rubbery concentrate is produced. If the concentrate is produced under conditions where it is rubbery, it may be extruded in the form of ribbons, rather than cylindrical strands, and subsequently cut into slivers.

Polyethylene/acrylic acid copolymers and ethylene/vinyl acetate/carbon monoxide terpolymers also exhibit good compatibility with a variety of biocides, including the more important biocides presently used in end use thermoplastic resin compositions. In addition to OBPA, biocides which may be stably incorporated into ethylene/acrylic acid copolymer or into ethylene/vinyl acetate/carbon monoxide terpolymer solid biocide resin concentrates at at least 20 times normal end use concentrations include, but are not limited to, N(2-methyl-1-naphthyl)malemid, such as that sold by Ventron under the trademark Vinyzene T-129 and 2-octyl, 4-isothiazolin-3-one, such as that sold under the trademark Skane M-8 by Rohm & Haas.

A further advantage of ethylene/acrylic acid copolymers as carriers of biocides is the high melt indicies of these polymers, typically being in the range of about 3000 under ASTM condition E at 190° C. Because the molten copolymer is highly fluid (non-viscous), the copolymer and the biocide carried thereby are rapidly mixed into a variety of molten thermoplastic resin compositions. For good mixing, the melt index of the resin or resins of the concentrate should be equal to or greater than the melt index of the primary resin and preferably should be in the range of 110% of the melt index of the primary resin.

In order that the solid biocide resin concentrate may be fabricated as a component of the end use resin compound, the solid biocide resin concentrate should have a softening temperature below or within the range of temperatures encountered during conventional processing of the primary thermoplastic resin used in the end use resin compound. These temperatures are within the range of between about 250° F. (137° C.) and about 500° F. (260° C.). It is preferred that the solid biocide resin concentrate have a softening temperature within a range of about 150° F. (65° C.) to about 300° F. (149° C.). Copolymers of ethylene and acrylic acid typically have softening temperatures within a range of about 176° F. (80° C.) to about 285° F. (140° C.).

Solid biocide resin concentrates according to this invention are prepared by mixing particulate thermoplastic resins with high concentrations of microbiocides such that homogeneous concentrates are obtained. The microbiocide and resins are mixed to obtain a dry homogeneous particulate composition. Thereafter, the composition is heated and mixed so that the resin is melted to a homogeneous composition to obtain a solution or dispersion of the microbiocide in the resin. The heated mixture is subjected to shear forces in any suitable apparatus, such as a two-roll mill or a Banbury mixer or extruder, and the resultant softened concentrate is formed, such as by extrusion, milling or calendering. The formed concentrate is cooled below the softening point so that it can be broken up into small particles, thereby permitting its subsequent mixing into the blend comprising the end use thermoplastic resin compound having an effective low concentration of the microbiocides. Upon cooling, the microbiocide is rendered far less migratory by the resin matrix.

An optional component of the end use compound is a plasticizer which gives the end use resin composition desired elastomeric properties. Furthermore, inclusion of a plasticizer in the fabricated end use resin composition may enhance biocide mobility in the end use resin composition.

Some mobility of the biocide is necessary in order that it be biologically active in the end use resin composition and for the biocide to be continuously replenished at the surfaces of the end use resin composition. Some resins, such as polyethylene, are sufficiently amorphous that the biocide is active and mobile without plasticizers. Other resins, such as PVC, require plasticizers for biocide activity and mobility. Any of conventional plasticizers can be employed, including, but not limited to diakyl phthalates, epoxy plasticizers, polyester plasticizers, diakyl phosphite and the like.

In addition, usual resin additives are included, such as ultraviolet stabilizers, heat stabilizers, fillers, dyes, pigments, lubricants and the like.

For forming the end use resin compositions, solid biocide resin concentrates are blended with particles of the primary thermoplastic resin and other components of an end use resin compound. The end use resin compound is fabricated in any conventional manner, such as extrusion, melting or calendering.

Small proportions of any of the additives included in the end use resin compound may be pre-included in the solid biocide resin concentrate, providing that a solid concentrate is formed in which the biocide is immobilized. However, from the standpoint of immobilizing a relatively high concentration of biocide in a thermoplastic resin in as inexpensive manner as possible, it is generally preferred that the solid biocide resin concentrate consist essentially of the biocide and the thermoplastic resin or resins.

Various aspects of the present invention will now be described in greater detail by way of specific examples.

EXAMPLE 1

Several resins were evaluated for compatibility with the biocide OBPA. The resins treated were as follows:
A. Arvis 3000—A high melt flow polypropylene co-polymer (Melt Flow—3000
B. Zonester 100—A polyester wood resin
C. Primacor 5981—A copolymer of 80% ethylene and 20% acrylic acid
D. DP-208—A polystyrene resin
E. EMA-2207—A copolymer of 20% ethylene methyl acrylate in polyethylene
F. Polypropylene 300 melt index
G. Elvaloy copolymer All of the above resins were processed with 5% biocide (OBPA) using a ¾ inch extruder. A color was added to make any surface spew or incompatibility noticeable.

| Ingredients | % |
| --- | --- |
| Biocide OBPA | 5.0 |
| Color tracer pigment | 0.5 |
| Candidate resin | 94.5 |
| | 100.0% |

The following observations were made during processing on the ¾" single screw extruder.
A. Arvis 3000—Sample drips out of die. Strand was difficult to maintain.
B. Zonester 100—Very tacky. Strand was impossible to maintain.
C. Primacor 5981—Strand was rubbery and caused pulsing in the extruder - processing temperatures were low.
D. DP-208—No processing problems.
E. EMA-2207—No processing problems.
F. Polypropylene 300 melt index—Difficult to maintain strand.
G. Elvaloy—Processing problems, strand very sticky, impossible to maintain.

The extruded strands were chopped and stored in plastic bags for subsequent evaluation for compatibility with the OBPA biocide. After 3 weeks of room temperature aging, all of the resins except EMA-2207 showed good compatibility with OBPA; there were no signs of surface spewing. The EMA-2207 resin exhibited a coating of OBPA on the surface after aging.

EXAMPLE 2

The following polymers were selected for further study based on processing ease and compatibility with the OBPA biocide.
C. Primacor 5981
D. DP-208 polystyrene
E. EMA-2207 (for control purposes-spew)
F. Polypropylene 300 melt index
G. Elvaloy terpolymer The selected resins, known to process well and to exhibit little or no spew, were evaluated further for compatibility with OBPA biocide. Concentrates of 5% OBPA in the selected resins were washed with methanol by contacting 2.5 grams of pellets with 50 mls of methanol for 10 seconds. The methanol was then analyzed by the SDDC colorimetric method for the amount of OBPA extracted.

| Extraction of 5% OBPA Concentrate Pellets with Mathanol | |
| --- | --- |
| Sample-5% OBPA In | % of Available OBPA Extracted |
| Polypropylene 12 melt flow | 0.4 |
| Polypropylene 300 melt flow | 0.6 |
| Primacor 5981 | 0.5 |
| Elvaloy terpolymer | 1.0 |
| EMA (control) | 2.3 |
| Polypropylene 3000 melt index | 1.0 |

The EMA which shows visible surface spewing also shows very high extraction levels of the active OBPA. The most promising resins for alloying based upon these results are the Priacor 5981 and the Polypropylene 300 melt flow.

EXAMPLE 3

Resins were selected based on OBPA surface spewing, leachability and ease of processing for alloying with 70% polyethylene. The purpose for alloying with polyethylene was to improve OBPA compatibility and permanence with this polymer. OBPA spews in polyethylene at levels above 0.20%. However, polyethylene is a desirable carrier for concentrates intended for use in polyolefin applications.

| OBPA Methanol Extraction and Visual Examination of 5% OBPA and 70% PE Alloy and Non-Alloy Formulation | | |
| --- | --- | --- |
| Sample | % of Available OBPA Washed Off | Microscopic Examination Spewing @ 7 Days |
| Polypropylene 3000 MI | 1.0 | Spew |
| Polypropylene 3000 MI + 70% PE | 0.6 | Spew |
| Primacor 5981 | 0.5 | No Spew |
| Primacor 5981 + 70% PE | 0.8 | No Spew |
| DP-208 Polystyrene | None | No Spew |
| DP-208 Polystyrene + 70% PE | 0.8 | No Spew |
| EMA 2207 | 1.1 | Spewing |
| EMA 2207 + 70% PE | 2.4 | Spewing |

Based upon these results, Primacor 5981 and DP-208 are the most suitable for producing an alloy in polystyrene-based resin. However, DP-208 polystyrene shows signs of incomplete dispersion when added to the polyethylene host resin. This is not surprising because polystyrene has a higher melt temperature than polyethylene.

EXAMPLE 4

Alloy concentrates were prepared with 70% polyethylene, 5% OBPA, 0.5% color tracer and with 25% of the following resins:
Arvis 3000
Zonester 100
Primacor 5981
DP-208 Polystyrene
2207 EMA These alloys concentrates were added to 2 polyethylenes of different melt index. The polyethylenes used were NPE-831 (M.I. 9) and NPE-870 (M.I. 30). The mixtures were extruded into ribbons at the following conditions:

| Type | Zone 1 Temp. | Zone 2 Temp. | Zone 3 Temp. | Zone 4 Temp. | Screw Speed RPM | Extruder Die Type |
|---|---|---|---|---|---|---|
| Single Screw | 150° C. | 155° C. | 160° C. | 165° C. | 110–125 | Sheet |

All samples extruded well and had good dispersion of the colored solid biocides with the exception of the samples containing DP-208 polystyrene. There were signs of poor dispersion as indicated by red streaks in the ribbon when DP-208 polystyrene single resin or alloy formulations were used.

EXAMPLE 5

Solid resin biocide concentrates were prepared containing a color tracer and (A) a terpolymer of ethylene, vinyl acetate and carbon monoxide sold under the trade designation Elvaloy 741 or (B) an ethylene/acrylic acid copolymer sold under the trade designation Primacor 5981. Ingredients and processing conditions in the extruder are given below:

| Ingredients | % | Processing Conditions Temps. | | | |
|---|---|---|---|---|---|
| | | Zone 1 | Zone 2 | Zone 3 | Zone 4 |
| A. Elvaloy 741 | 94.5 | 100° C. | 105° C. | 110° C. | 115° C. |
| OBPA | 5.0 | | | | |
| Hostaprint HF36 | 0.5 | | | | |
| Red Pigment | | | | | |
| | 100.0 | | | | |

Screw Speed—100 RPM
Extruder—Single Screw
Die—⅜" strand

| Ingredients | % | Processing Conditions Temps. | | | |
|---|---|---|---|---|---|
| | | Zone 1 | Zone 2 | Zone 3 | Zone 4 |
| B. Promacor 5981 | 94.5 | 95° C. | 100° C. | 105° C. | 110° C. |
| OBPA | 5.0 | | | | |
| Hostaprint HF 36 | 0.5 | | | | |
| Red Pigment | | | | | |
| | 100.0 | | | | |

Running Speed—100 RPM
Extruder—Single Screw Die—⅜" strand

Both the Elvaloy and Primacor concentrates processed well; however the Elvaloy concentrate was more rubbery than desired for pelletization.

EXAMPLE 6

Each of the concentrates prepared in Example 5 were tested for compatibility with PVC/PVA (85:15). A polypropylene concentrate (SB-1-PR) was used as a negative control. In each case the PVC/PVA comprised 99 wt. percent and the concentrate 1%. Extruder conditions were as follows:

| | Processing Conditions | | | |
|---|---|---|---|---|
| | Zone 1 | Zone 2 | Zone 3 | Zone 4 |
| Temps. | 135° C. | 140° C. | 145° C. | 150° C. |

Running Speed—100 RPM
Extruder single screw
Die—4 in. sheet die
Die—4 inch sheet die In the PVC/PVA copolymer ribbon produced, the Primacor concentrate showed full compatibility with no streaks due to undispersed color tracer. In the Elvaloy-containing ribbon, some phase separation was present which was attributed to temperature ranges below that which is optimal for Elvaloy addition; however, dispersion was sufficient to demonstrate compatibility of PVC/PVA with Elvaloy. The propylene control proved to be completely incompatible with PVC/PVA as evidenced by read streaks.

EXAMPLE 7

Each of the concentrates prepared in Example 5 were tested for compatibility with polypropylene (Hercules 6323) (1 part concentrate to 99 parts polyprolylene). Processing conditions in the extruder were as follows:

| | Processing Conditions | | | |
|---|---|---|---|---|
| | Zone 1 | Zone 2 | Zone 3 | Zone 4 |
| Temps. | 200° C. | 205° C. | 210° C. | 210° C. |

Both Primacor and Elvaloy show good dispersion and compatibility with polypropylene as evidenced by the even color and smooth surface of the extruded test ribbon.

EXAMPLE 8

Each of the concentrates prepared in Example 5 were tested for compatibility with polystyrene (DP-208) (1 part concentrate to 99 pats polystyrene). Processing conditions in the extruder were as follows:

| | Processing Conditions | | | |
|---|---|---|---|---|
| | Zone 1 | Zone 2 | Zone 3 | Zone 4 |
| Temps. | 200° C. | 205° C. | 210° C. | 220° C. |

Running Speed—125 RPM
Extruder—single screw
Die-4 in. sheet die

Both concentrates show good dispersion and compatibility with polystyrene.

EXAMPLE 9

Each of the concentrates prepared in Example 5 were tested for compatibility with nylon (Allied LPSN nylon) (1 part concentrate to 99 parts polystyrene). Processing conditions in the extruder were as follows:

| | Processing Conditions | | | |
|---|---|---|---|---|
| | Zone 1 | Zone 2 | Zone 3 | Zone 4 |
| Temps. | 250° C. | 260° C. | 260° C. | 250° C. |

Running Speed—100 RPM
Extruder single screw
Die—4 in. sheet die

Both Primacor and Elvaloy are compatible with nylon resin.

While the invention has been described in terms of certain preferred embodiments, modifications obvious to one with ordinary skill in the art may be made without departing from the scope of the invention; for example, although the invention has been described particularly with respect to solving a particular biocide/resin compatibility problem, i.e., OBPA with polyethylene resins, other biocide/resin compatibility problems may be addressed in a similar manner.

Various features of the invention are recited in the following claims.

We claim:

1. A solid biocide resin concentrate for supplying to an end use resin composition of which a primary thermoplastic resin comprises a major proportion, comprising a biocide in an amount which is effective to protect the end use resin composition from microorganism attack, the solid biocide resin concentrate comprising (1) a first thermoplastic resin identical to or substantially identical to said primary thermoplastic resin, said first thermoplastic resin being incompatible with stable incorporation of said biocide at 20 times end use concentration, (2) an alloyed second thermoplastic resin and (3) a biocide, selected from the group consisting of 10,10'-oxybisphenoxarsine and its derivatives, N(2-methyl-1-naphthyl) malemid and 2-octyl, 4-isothiazolin-3-one, stably incorporated and immobilized in said alloyed resins at a concentration of at least about 20 times end use concentration; said first thermoplastic resin being selected form the group consisting of polyethylene, nylon, polystyrene, polyvinyl chloride, polycarbonate, polypropylene, polyvinylchloride/polyvinyl acetate copolymer, polyvinyl, acetate and polymethyl methacrylate, and providing that when said first thermoplastic resin is polyethylene, said second thermoplastic resin is selected from the group consisting of ethylene/acrylic acid copolymer, polypropylene, polystyrene, polyvinyl chloride/polyvinyl acetate copolymer, polyacrylic acid and ethylene/vinyl acetate/carbon monoxide terpolymer; and providing that when said first thermoplastic resin is selected from the group consisting of nylon, polystyrene, polyvinyl chloride, polycarbonate, polypropylene, polyvinyl chloride/polyvinyl acetate copolymer, polyvinyl acetate and polymethyl methacrylate, said second thermoplastic resin is selected from the group consisting of ethylene/acrylic acid copolymer and ethylene/vinyl acetate/carbon monoxide terpolymer.

2. A solid biocide resin concentrate in accordance with claim 1 wherein said first thermoplastic resin comprises at least about 50 weight percent of said alloyed resins.

3. A solid biocide resin concentrate according to claim 1 wherein said second resin is a copolymer of ethylene and acrylic acid, comprising between about 3 and about 25 molar percent acrylic acid mer units, balance ethylene mer units.

4. A solid biocide resin concentrate according to claim 1 wherein said biocide is selected from the group consisting of 10,10'-oxybisphenoxarsine, N(2-methyl-1-naphthyl)maleimid and 2-octyl,4-isothiazolin-3-one.

5. A solid biocide resin concentrate according to claim 1 wherein said biocide is 10,10'-oxybisphenoxyarsine.

6. A solid biocide resin concentrate comprising a thermoplastic resin or resin mixture, between about 30 and 100 wt. percent of which comprises (A) a copolymer of ethylene and acrylic acid, acrylic acid mer units comprising between about 3 and about 25 molar percent of the mer units of said copolymer, (B) balance of said resin mixture being another thermoplastic resin selected from the group consisting of polyethylene, nylon, polystyrene, polyvinyl chloride, polycarbonate, polypropylene, polyvinyl chloride/polyvinyl acetate copoplymer, polyvinyl acetate and polymethyl methacrylate, and (C) a biocide, selected from the group consisting of 10,10'-oxybisphenoxarsine and its derivatives, N(2-methyl-1-naphthyl) malemid and 2-octyl, 4-isothiazolin-3-one, stably incorporated and immobilized therein, the concentration of biocide in said solid biocide resin concentrate being at least about 20 times the concentration of biocide generally employed in end use resin compositions.

7. A solid biocide resin concentrate in accordance with claim 6 wherein said biocide is 10,10'-oxybisphenoxarsine and is present at least about 1% by weight of said resin or resin mixture.

8. A solid biocide resin concentrate according to claim 6 wherein said thermoplastic resin consists essentially of said ethylene/acrylic acid copolymer.

9. A solid biocide resin concentrate comprising a thermoplatic resin or resin mixture, between about 30 and 100 wt. percent of which comprises (A) a terpolymer consisting essentially of between about 40 and about 75 molar percent ethylene mer units, between about 20 and about 30 molar percent vinyl acetate mer units and between about 5 and about 35 molar percent carbon monoxide mer units, (B) balance of said resin mixture being another thermoplastic resin selected from the group consisting of polyethylene, nylon, polystyrene, polyvinyl chloride, polycarbonante, polypropylene, polyvinyl chloride/polyvinyl acetate copolymer, polyvinyl acetate and polymethyl methacrylate, plus (C) a biocide, selected from the group consisting of 10,10'-oxybisphenoxarsine and its derivaties, N(2-methyl-1-naphthyl) malemid and 2-octyl, 4-isothiazolin-3-one, stably incorporated and immobilized therein, the concentration of biocide in said solid biocide resin concentrate being at least about 20 times the concentration of biocide generally employed in end use resin compositions.

10. A solid biocide resin concentrate in accordance with claim 9 wherein said biocide is 10,10'-oxybisphenoxarsine and is present at at least by weight of said resin or resin mixture.

11. A solid biocide resin concentrate according to claim 9 wherein said thermoplastic resin consists essentially of said ethylene/vinyl acetate/carbon monoxide terpolymer.

12. A solid biocide resin concentrate for supplying, to an end use resin composition in which a primary thermoplastic resin comprises a major proportion, comprising a biocide in an amount which is effective to protect the end use resin composition from microorganism attack, said primary resin being a polyethylene homopolymer, said primary polyethylene resin being incompatible with stable incorporation of the biocide at 20 times end use concentration, the solid biocide resin concentrate comprising a first thermoplastic resin, selected form the group consisting of ethylene acrylic acid copolymer and ethylene/vinyl acetate/carbon monoxide terpolymer, said first thermoplastic resin being present in said solid resin composition either (A) as the sole thermoplastic resin component or (B) in combination with a thermoplastic polyethylene resin, plus, the biocide, selected from the group consisting of 10,10'-oxybisphenoxarsine and its derivatives, N(2-methyl-1-naphthyl malemid and 2-octyl, 4-isothiazolin-3-one, stably incoporated into said thermoplastic resin or resins at a weight percent relative to said resin or resins of at least about 20 times the concentration of biocide in the end use resin composition.

13. A solid biocide resin concentrate in accordance with claim 12 wherein mer units, selected from the group consisting of (a) acrylic acid mer units and (b) vinyl acetate plus carbon monozide mer units, comprise between about 3 and about 50 molar percent of the total mer units of said resin or resins.

14. A method of preparing a biocide-containing end use resin composition, the major component of which is a primary thermoplastic resin in which the biocide cannot be stably incorporated and immobilized at 20 times or more normal end use concentration, the method comprising providing (1) particulates of a first thermoplastic resin identical to or substantially identical to said primary thermoplastic resin, (2) particulates of a second thermoplastic resin having good compatiblity with the biocide and (3) the biocide, selected from the group consisting of 10,10'-oxybisphenoxarsine and its derivative, N(2-methyl-1-naphthyl) malemid and 2-octyl, 4-isothiazolin-3-one, at a percent by weight of said thermoplastic resins at least about 20 times the normal weight percent relative to resin components of the end use resin composition; said first thermoplastic resin being selected from the group consisting of polyethylene, nylon, polystyrene, polyvinyl chloride, polycarbonate, polypropylene, polyvinylchloride/polyvinyl acetate copolymer, polyvinyl acetate and polymethyl methacrylate, and providing that when said first thermoplastic resin is polyethylene, said second thermoplastic resin is selected from the group consisting of ethylene/acrylic acid copolymer, polypropylene, polystyrene, polyvinyl chloride/-polyvinyl acetate copolymer, polyacrylic acid and ethylene/vinyl acetate/carbon monoxide terpolymer; and providing that when said first thermoplastic resin is selected from the group consisting of nylon, polystyrene, polyvinyl chloride, polycarbonate, polypropylene, polyvinyl chloride/polyvinyl acetate copolymer, polyvinyl acetate and polymethyl methacrylate, said second thermoplastic resin is selected from the group consisting of ethylene/acrylic acid copolymer and ethylene/vinyl acetate/carbon monoxide terpolymer, fusing said first and second resins and said biocide to form a solid biocide resin concentrate in which said biocide is stably incorporated and immobilized, forming particles of said solid biocide resin concentrate, mixing particulates of the primary resin and said particles of said solid biocide resin concentrate plus either no additional components or additional components selected from the group consisting of plasticizers, ultraviolet stabilizers, heat stabilizers, fillers, dyes, pigments, lubricants and mixtures thereof to form an end use resin compound, and fabricating said end use resin compound into the end use resin composition.

15. A method of preparing a biocide-containing end use resin composition comprising providing a primary thermoplastic resin selected from the group consisting of polyethylene, polystyrene, polyvinyl chloride, polycarbonate, polypropylene, polyvinyl chloride/polyvinyl acetate copolymer, polyvinyl acetate and polymethyl methacrylate, mixing thermoplastic resin particulates, (1) between about 30 and 100 wt. percent of which are either (a) a copolymer of ehtylene and acrylic acid with acrylic acid mer units comprising between about 3 and about 25 molar percent or (b) a terpolymer of ethylene, vinyl acetate and carbon monoxide, wherein between about 40 and about 75 molar percent of the mer units are ethylene, between about 20 and about 30 molar pecent of the mer units are vinyl acetate and between about 5 and about 35 molar percent of the mer units are carbon monoxide, (2) balance a thermoplastic resin substantially identical to said primary resin and (3), the biocide, selected from the group consisting of 10,10'-oxybisphenoxarsine and its derivatives, N(2-methyl-1-naphtyl) malemid and 2-octyl, 4-isothiazolin-3-one, at a percent by weight of said thermoplastic resins which is at least about 20 times the normal weight percent relative to thermoplastic resin components of the end use resin composition, fusing said thermoplastic resin particulates and said biocide to form a solid biocide resin concentrate in which said biocide is stably incorporated and immobilized, forming particles of said solid biocide resin concentrate, mixing particulates of said primary thermoplastic resin, said particles of said solid biocide resin concentrate plus either no additional components or additional components selected from the group consisting of plasticizers, ultraviolet stabilizers, heat stabilizers, fillers, dyes, pigments, lubricants and mixtures thereof to form an end use resin compound, and fabricating said end use resin compound into the end use resin composition.

16. A method according to claim 15 wherein said thermoplastic resin particulates consist either essentially of said ethylene/acrylic copolymer or essentially of said ethylene/vinyl acetate/carbon monoxide terpolymer.

17. A method of preparing a biocide-containing end use resin composition, a major portion of which is a primary homopolymeric polyethylene thermoplastic resin in which the biocide cannot be stably incorporated and immobilized at 20 times or more normal weight percent relative to thermoplastics in the end use resin composition, the method comprising providing particulates of a first thermoplastic resin selected form the group consisting of ethylene/a-crylic acid copolymer and ethylene/vinyl acetate/-carbon monoxide terpolymer, mixing (1) from about 30 to 100 wt percent particulates of said first resin, (2) balance, thermoplastic polyethylene resin, and (3), the biocide, selected from the group consisting of 10,10'-oxybisphenoxarsine and its derivatives, N(2-methyl-1-naphthyl) malemid and 2-octyl, 4-isothiazolin-3-one, at a percent by weight relative to said thermoplastic resins at least about 20 times the normal end use wt. percent of biocide relative to thermoplastic resins in the end use resin composition, fusing said resins particulates and said biocide to form a solid biocide resin concentrate in which said biocide is stably incorporated and immobilized, forming particles of said solid biocide resin concentrate, mixing particulates of the primary resin, said particles of said solid biocide resin concentrate plus either no additional components or additional components selected form the group consisting of plasticizers, ultraviolet stabilizers, heat stabilizers, fillers, dyes, pigments, lubricants and mixtures thereof to form an end use resin compound, and fabricating said end use resin compound into the end use resin composition.

18. A solid biocide resin concentrate according to claim 1 wherein said second resin is either (a) a terpolymer of ethylene, vinyl acette and carbon monoxide, or (b) an ethylene/acrylic acid copolymer, said first thermoplastic resin comprising at least about 50 weight percent of said alloyed resins, said second resin comprising at least about 30 weight percent of said alloyed resins.

19. A method according to claim 14 wherein said second resin is either (a) a terpolymer of ethylene, vinyl acetate and carbon monoxide or (b) an ethylene/acrylic acid copolymer, said first thermoplastic resin comprising at least about 50 weight percent of said alloyed resins, said second resin comprising at least about 30 weight percent of said alloyed resins.

* * * * *

UNITED STATES PATENT AND TRADEMARK OFFICE
CERTIFICATE OF CORRECTION

PATENT NO. : 4,789,692
DATED : Dec. 6, 1988
INVENTOR(S) : Nuno M. Rei et al

It is certified that error appears in the above-identified patent and that said Letters Patent is hereby corrected as shown below:

Column 2, line 50, delete "an" and insert --can--.
Column 3, line 20, delete "sold" and insert --solid--.
Column 14, line 2, delete whole line, is a duplication.
Column 14, after table in Example 7, insert --
    Running Speed--125 RPM
    Extruder--single screw
    Die--4 inch sheet die--.

Column 16, line 42, after "least" insert --about 1%--.

Column 19, line 10, substitute "acette" with --acetate--.

Signed and Sealed this

First Day of October, 1991

*Attest:*

HARRY F. MANBECK, JR.

*Attesting Officer*      *Commissioner of Patents and Trademarks*